(12) United States Patent
Blankenstein et al.

(10) Patent No.: US 7,736,907 B2
(45) Date of Patent: Jun. 15, 2010

(54) DEVICE FOR COLLECTING BLOOD AND SEPARATING BLOOD CONSTITUENTS, METHOD FOR SEPARATING BLOOD CONSTITUENTS AND USE OF SAID DEVICE

(75) Inventors: Gert Blankenstein, Dortmund (DE); Ralf-Peter Peters, Bergisch-Gladbach (DE)

(73) Assignee: Boehringer Ingelheim microParts GmbH, Dortmund (DE)

( * ) Notice: Subject to any disclaimer, the term of this patent is extended or adjusted under 35 U.S.C. 154(b) by 734 days.

(21) Appl. No.: 11/569,999

(22) PCT Filed: Jun. 3, 2005

(86) PCT No.: PCT/EP2005/005982

§ 371 (c)(1),
(2), (4) Date: Dec. 4, 2006

(87) PCT Pub. No.: WO2005/119211

PCT Pub. Date: Dec. 15, 2005

(65) Prior Publication Data

US 2007/0269893 A1    Nov. 22, 2007

(30) Foreign Application Priority Data

Jun. 4, 2004    (DE) .................. 10 2004 027 422

(51) Int. Cl.
*G01N 33/50* (2006.01)
(52) U.S. Cl. .................. 436/177; 436/2; 436/165; 436/524; 436/531; 422/58; 422/61; 422/82.05; 210/782
(58) Field of Classification Search .................. 422/58, 422/61, 82.05; 436/524, 531, 165, 2, 177; 210/782

See application file for complete search history.

(56) References Cited

U.S. PATENT DOCUMENTS

| 4,302,313 | A | | 11/1981 | Columbus |
| 4,426,451 | A | * | 1/1984 | Columbus .................. 436/518 |
| 4,883,688 | A | | 11/1989 | Houts et al. |
| 4,906,439 | A | | 3/1990 | Grenner |
| 5,051,237 | A | | 9/1991 | Grenner et al. |
| 5,230,866 | A | | 7/1993 | Shartle et al. |
| 5,350,694 | A | * | 9/1994 | Zimmerle ................ 436/2 |
| 5,397,538 | A | * | 3/1995 | Stark et al. .................. 422/57 |
| 5,885,527 | A | | 3/1999 | Buechler |
| 6,156,270 | A | * | 12/2000 | Buechler ................ 422/58 |

(Continued)

FOREIGN PATENT DOCUMENTS

DE    19810499 A1    9/1999

(Continued)

*Primary Examiner*—Robert J Hill, Jr.
*Assistant Examiner*—Dwan A Gerido
(74) *Attorney, Agent, or Firm*—David S. Safran; Roberts Mlotkowski Safran & Cole, P.C.

(57) ABSTRACT

A device and a method for collecting blood and separating blood plasma as a liquid sample using a channel that absorbs the liquid sample by capillary forces. To obtain a uniform filling of the channel with the liquid sample and an effective separation, deaeration takes place in a transverse direction to the main filling direction or to the longitudinal direction of the channel, immediately downstream of a separation device in an inlet region of the channel.

45 Claims, 7 Drawing Sheets

U.S. PATENT DOCUMENTS

| | | |
|---|---|---|
| 6,271,040 B1 * | 8/2001 | Buechler .................... 436/170 |
| 6,296,126 B1 | 10/2001 | Peters |
| 6,391,265 B1 * | 5/2002 | Buechler et al. ............ 422/101 |
| 6,540,962 B1 | 4/2003 | Okubo et al. |
| 6,592,815 B1 | 7/2003 | Zimmer |
| 2003/0031593 A1 | 2/2003 | Okubo et al. |

FOREIGN PATENT DOCUMENTS

| | | |
|---|---|---|
| DE | 10142788 A1 | 3/2003 |
| EP | 1201304 A2 | 5/2002 |
| WO | 9956878 A1 | 11/1999 |
| WO | 0124931 A1 | 4/2001 |

* cited by examiner

DEVICE FOR COLLECTING BLOOD AND SEPARATING BLOOD CONSTITUENTS, METHOD FOR SEPARATING BLOOD CONSTITUENTS AND USE OF SAID DEVICE

BACKGROUND OF THE INVENTION

1. Field of the Invention

The present invention relates to microfluidic systems and devices and, more particularly, to a device for collecting blood and separating blood constituents, such as blood plasma, as a sample liquid, in which capillary forces are used and are critical in particular for the function. The present invention also relates to a method of separating blood constituents and to uses of the device for determining an intracellular parameter or for detecting one or more blood constituents.

2. Description of Related Art

A device for separating liquid components is known from EP 1 013 341 A2, which constitutes the starting point for the present invention, wherein for example blood plasma as a sample liquid is separated from the blood in a filter or a membrane and is collected by capillary forces in a collecting chamber or channel for diagnostic purposes. The channel has a substantially rectangular cross-section. It is formed in a carrier by a corresponding recess covered at the top. In addition, the channel has wedge-shaped notches as guide elements to ensure total filling of the increasing cross-section channel with the sample liquid. However, the design for the channel still does not ensure optimum filling with the sample liquid.

U.S. Pat. No. 4,906,439 and International Patent Application Publication WO 01/24931 A1 both disclose devices for separating blood plasma from blood, wherein a plurality of groove- or capillary-like individual channels are provided for collecting and carrying away the blood plasma. The disadvantage arises that the channels fill up with the sample liquid in the form of blood plasma at different rates or not at all. Accordingly, it is not possible to achieve a uniform liquid front. This is disadvantageous in terms of the diagnosis as there are no defined quantities available simultaneously or, for example, dry chemicals or the like cannot simultaneously be dissolved by the sample liquid to the desired or necessary extent.

SUMMARY OF THE INVENTION

The object of the present invention is to provide a device for collecting blood and separating blood constituents, such as blood plasma, as a sample liquid, a method of separating blood constituents, and uses of the device for easy and rapid determination of plasma constituents and/or of an intracellular parameter, enabling optimum separation of the blood constituents and filling of a channel with sample liquid and, preferably, improving the possibilities of diagnosis or investigation.

A fundamental idea of the present invention is to vent the sample liquid in the inlet region of the channel, which is immediately adjacent to the separator on the outflow side, at right-angles to the main filling direction of the channel with sample liquid and/or at right-angles to the longitudinal extent of the channel.

The proposed venting allows optimum uniform filling of the channel, particularly in the inlet region, and prevents undesirable effects of air.

The proposed venting also allows particularly efficient blood separation. When air is trapped at the separator on the outflow side, this trapped air blocks the discharge of sample liquid from the separator. Accordingly, in this case, only those parts of the separator which are not blocked by trapped air are able to carry out the separation of the sample liquid. The trapped air is unable to escape through the separator, particularly a gas-permeable membrane or other filter element, as the blood which is to be separated usually covers the whole of the separator on the inflow side and accordingly prevents venting. The proposed venting allows a discharge and, hence, prevention of such trapped air on the outflow side of the separator, so that the separator is optimally used to separate blood and as a result effective and rapid blood separation takes place.

The venting device is preferably designed to vent the sample liquid directly on the outflow side of the separator. In particular, the venting device is designed to vent the sample liquid in the inlet region in the main plane of extension of the channel and/or along a flat side of the separator and/or at right-angles to the flow device for the sample liquid through the separator. This enables effective venting of the inlet region of the channel.

Preferably, the venting device comprises at least one transverse channel in the inlet area extending transversely of the main filling direction of the channel. A number of parallel transverse channels may also be provided. This is a simple method of ensuring effective venting.

Alternatively, or additionally, the channel may be open at the side, at least in the inlet area—particularly along the longitudinal or narrow sides—in order to achieve the proposed venting in the inlet area.

In particular, the channel is then constructed to be open at opposite longitudinal or narrow sides of the inlet area, to achieve a particularly effective venting of the sample liquid in the inlet area and prevent trapped air on the outflow side of the separator.

Preferably, the sample liquid is collected by capillary forces in the channel, which is open at least along a narrow side or longitudinal side, so as to form a lateral liquid stop for the sample liquid in the channel and so that the sample liquid can pass through the channel without any sidewalls. In particular, a recess is laterally adjacent to the open side of the channel.

The laterally open construction of the channel provides improved and particularly optimum venting when filling the channel with sample fluid, particularly both in the inlet region and in other channel regions.

Guiding without sidewalls is a simple way of preventing the sample liquid from rushing forwards, i.e. filling the channel rapidly, where a sidewall would normally be present. This makes it possible to even out the filling speed over the entire cross-section of the channel, so that an at least substantially uniform or straight liquid front can be achieved when filling the channel. This also allows optimum, uniform filling of the channel and prevents undesirable trapped air. However, other measures may also be provided for preventing sample liquid from rushing forwards along the narrow or longitudinal sides of the channel, such as a suitably modified sidewall, e.g. provided with elevations.

Moreover, the surface of the sample liquid held or guided without any sidewalls allows direct investigation of the sample liquid, particularly by the introduction of light, without a sidewall or the like which would otherwise be present.

A proposed use of the device is characterized in that lysing is carried out directly by means of a first chemical and immediately afterwards the intracellular parameter is determined using a second chemical. This allows quick and cheap analysis or determination of the parameter while achieving a simple and compact structure.

Another proposed use of the device is characterized in that immediately after the blood cells have been retained or separated off, a constituent or parameter of the blood plasma can be determined directly using a chemical or a number of chemicals. This allows quick and inexpensive analysis or determination of the parameter while maintaining a simple and compact structure.

Further advantages, features, properties and aspects of the present invention will become apparent from the claims and the following description of preferred embodiments shown in the drawings.

BRIEF DESCRIPTION OF THE DRAWINGS

FIG. 2a is a schematic plan view of a carrier of the filled device according to FIG. 1;

FIG. 2b shows an enlarged detail of FIG. 2a;

FIG. 3 is a schematic section through the device on the line III-III in FIG. 2a;

FIG. 4 is a schematic longitudinal section through the device on the line IV-IV in FIG. 2a;

FIG. 8 is a schematic longitudinal section through a proposed device according to a fourth embodiment;

FIG. 9a is a schematic section through a proposed device according to a fifth embodiment;

FIG. 9b is an enlargement of a detail of FIG. 9a;

DETAILED DESCRIPTION OF THE INVENTION

In the Figures, the same reference numerals are used for identical or similar parts, and comparable or equivalent properties and advantages are achieved even if the description is not repeated.

Figure 1:
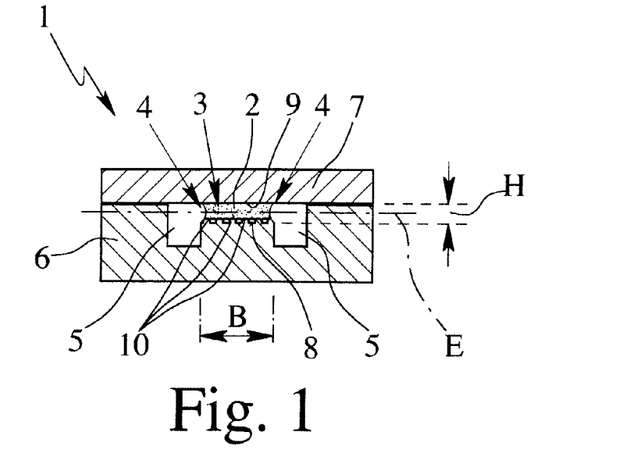
FIG. 1 is a schematic section on the line I-I in FIG. 2a through a proposed device for collecting blood and separating blood components according to a first embodiment.

FIG. 1 shows a schematic section through a first embodiment of a proposed device 1 for collecting and/or diagnosing a sample liquid 2, particularly blood plasma or the like.

The device 1 has a channel 3, which collects the sample liquid 2 by capillary forces. The channel 3 is open in construction, at least on a narrow side or longitudinal side 4, in this embodiment on both narrow or longitudinal sides 4, as shown in FIG. 1.

Laterally adjoining the open sides 4 is a recess 5 which is preferably groove- or trench-shaped in the embodiment. A lateral liquid stop for the sample liquid 2—i.e. an obstacle to flow which cannot be overcome by capillary forces—is formed in the channel 3 and the sample liquid 2 can be guided along the open sides 4 in the channel 3 without any sidewalls.

In the embodiment shown, the device 1 has a carrier 6 and an associated cover 7 between which are formed the channel 3 and the recess 5. If necessary, only portions of the carrier 6 are removed in order to form the required structures and the cover 7 is of smooth construction, but preferably at least substantially free from recesses. However, the reverse may also be true. If necessary, however, portions of both the carrier 6 and the cover 7 may be removed and/or constructed with projections to form the desired structures and optionally to hold chemicals, reagents, investigation devices or the like which are not shown here.

The recess 5 preferably adjoins the channel 3 with a sharp edge, as shown in FIG. 1. In the embodiment, by way of example, the recess 5 is formed only in the carrier 6 and, in the representation shown in FIG. 1, it extends only downwards in relation to a lateral projection of the channel 3. However, the recess 5 may extend upwards or on both sides of the lateral projection of the channel 3, i.e. in particular upwards and downwards, as desired.

The recess 5 which is preferably rectangular in cross-section leads to such an increase in cross-section, particularly a step or sudden increase, that the capillary forces are reduced such that the above-mentioned liquid stop for the sample liquid 2 is formed in the transition from the channel 3 to the recess 5, as indicated in FIG. 1.

The channel 3 is preferably defined or formed by only two opposing, especially substantially flat surfaces or flat sides 8 and 9, which are formed by the carrier 6 or cover 7 in the embodiment shown and run parallel to one another. If necessary, therefore, the recess 5 may be omitted altogether and the channel 3 may be formed, for example, by two suitable bars or the like at a suitable spacing to generate the required capillary forces FIG. 2a shows a schematic plan view of the carrier 6 of the device 1 without a cover 7, but partly filled by the sample liquid 2 up to the liquid front V.

In the embodiment shown, the recess 5 extends along the open side or sides 4 of the channel 3, preferably at least along opposing open longitudinal sides 4. Moreover, in the embodiment shown, the channel 3 is designed to be open laterally on all sides and the recess 5 is accordingly constructed to surround it. The channel 3 is thus entirely surrounded by the recess 5.

Figures 2A, 2B:
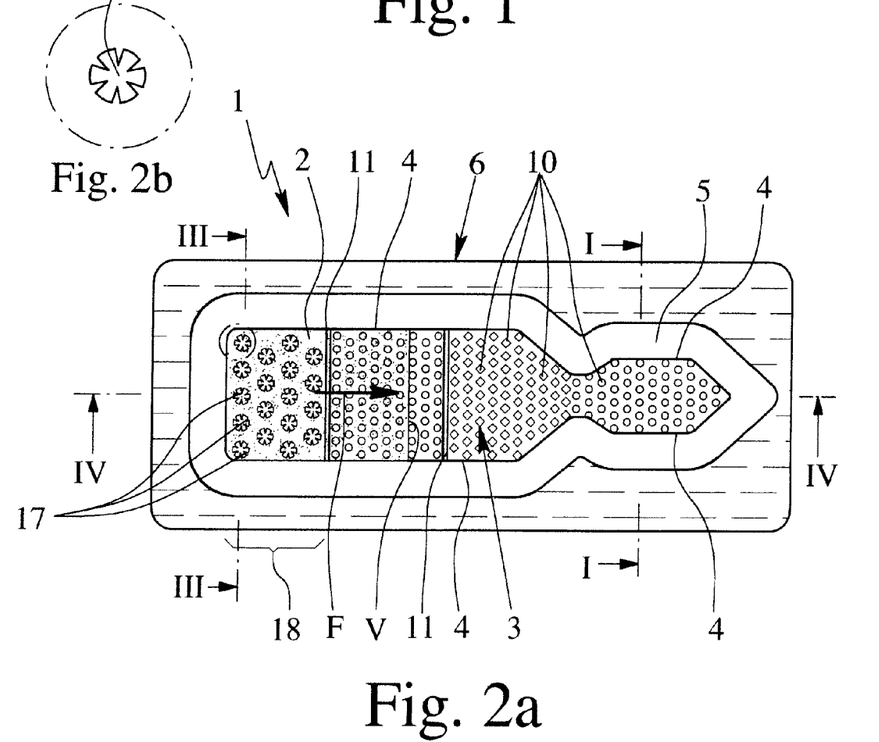

Preferably, the recess 5 is adjacent to the narrow sides or longitudinal sides 4 of the channel which extend at least substantially parallel to the main direction of filling F of the channel 3 with sample liquid 2 (main direction of flow of the sample liquid 2 in the channel 3), as indicated in FIG. 2a. Consequently, the recess 5 preferably extends at least partly parallel to the main filling direction F.

According to another alternative embodiment, which will be described hereinafter with reference to FIG. 9a, it is also possible for the recess 5 to fill up with the sample liquid 2 or some other liquid which does not mix with the sample liquid 2, in particular, such as oil or the like. In this case the recess 5 or the sidewall of the channel 3, however, is designed so that the fill speed is at most as great as the fill speed of the channel 3, to achieve the most uniform possible filling with sample liquid 2. The fill speeds refer to the filling or advancing of the liquid front V in the main direction of filling F.

Alternatively, the recess 5 may also simply be rinsed with the other liquid before the sample liquid 2 is introduced.

The channel 3 preferably has a substantially rectangular and/or flat cross-section, more particularly at right-angles to the main filling direction F.

The height H of the channel 3 indicated in FIG. 1—i.e. the spacing between the preferably parallel surfaces 8 and 9 which delimit the channel 3—is not more than 2000 μm, preferably not more than 500 μm, in particular about 50 to 200 μm. The recess 5 preferably leads to a stepwise or sudden increase in the height H and hence to the formation of the desired liquid stop. In particular the height H of the recess 5 is at least twice as great as the height H of the channel 3.

The width B of the channel 3 is preferably about 100 to 5000 μm, in particular about 200 to 4000 μm.

The height H of the channel 3 is substantially less, in particular by at least a factor of 5 or 10, than the width B of the channel 3.

The capacity of the channel 3 is preferably less than 1 ml, particularly less than 100 μl, more preferably not more than 10 μl.

The device 1 thus forms a microfluidic system. In particular, the device 1 can be used for microfluidic diagnosis for medical or non-medical purposes or other investigations.

The channel 3 and hence its main filling direction F and main extension plane E preferably run at least substantially horizontally in the position of use. However, depending on the intended use or constructional solution, another alignment is also possible, particularly as the collection or filling of the channel 3 with sample liquid 2 is, preferably, at least primarily determined or brought about solely by capillary forces. Thus, the main direction of filling F may run horizontally or at a slope, for example, while the main extension plane E runs vertically, for example, so that the channel 3 is also aligned vertically.

The channel 3 preferably forms at least one reservoir for the sample liquid 2, particularly for diagnostic purposes. If desired the channel 3 may contain a chemical, particularly a dry chemical or the like, not shown here. However, investigations on the sample liquid 2 may also be carried out in other ways.

In the embodiment shown the channel 3 has at least one guide element for influencing and particularly for evening out the filling with the sample liquid 2.

According to an alternative embodiment, the channel 3 has preferably regularly distributed elevations 10 as guide elements. These are arranged, in particular, in rows at right-angles to, preferably perpendicularly, or longitudinally with respect to the main direction of filling F, particularly alternately offset in the transverse direction. The elevations 10 are offset in the main direction of filling F in the rows. This allows the sample liquid 2 to fill the channel 3 in rows, i.e. row by row, and in this way to advance with a substantially straight liquid front V in the main direction of filling F.

If required, the surface density, the spacing and/or the size of the elevations 10 can vary, particularly as a function of their respective distance from an inlet (not shown in FIGS. 1 and 2) for the sample liquid 2 into the channel 3.

The elevations 10 are preferably in the form of bars, bumps or columns, particularly with a round or polygonal base area. However, depressions could also be provided instead.

Alternatively or additionally, the channel 3 may have at least one trench 11 or bar as the guide element, extending transversely or longitudinally with respect to the main direction of filling F of the channel 3. The groove-live trench 11 preferably provided, which is more particularly rectangular or semicircular in cross-section, has a substantially smaller depth than the recess 5 and therefore forms only a temporary liquid stop for evening out the liquid front V. This ensures that the sample liquid 2 does not fill the trench 11 and, thereafter, the subsequent channel region until it has filled the channel 3 over its entire cross-section.

It should be emphasized that by combining the guide elements with the guiding of the sample liquid 2 without the use of sidewalls, it is possible to achieve highly uniform filling of the channel 3 by capillary forces with a liquid front V extending at least substantially straight or at right-angles to the main direction of filling F.

Alternatively, the channel 3 and/or a reservoir, collecting chamber, collecting region or the like formed thereby may also be at least substantially smooth or even, i.e. in particular with no guide elements.

Figure 3:
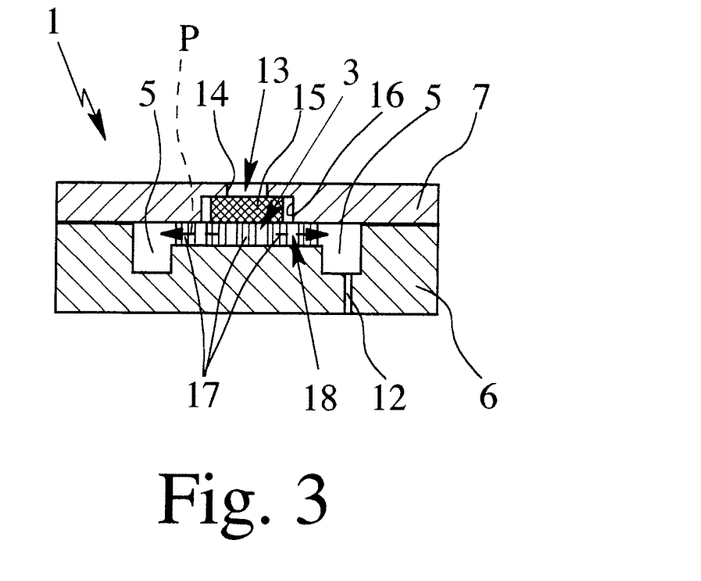

FIG. 3 shows another diagrammatic section through the device 1 with the cover 7 on the line III-III in FIG. 2a.

The device 1 in FIG. 3 comprises at least one venting channel 12 associated with the channel 3, which in the embodiment shown is not directly adjacent to the channel 3 but to the recess 5. Thus, no additional liquid stop is needed for the venting 12, to prevent sample liquid 2 from escaping through the vent 12. The design of the channel 3, which is preferably laterally open all round, allows optimum venting when the channel 3 is being filled with the sample liquid 2, so that undesirable trapped air can be reliably prevented.

The sample liquid 2 can be supplied to the channel 3 preferably perpendicularly to the direction of the channel 3, particularly in the vertical direction in the position of use.

Figure 4:
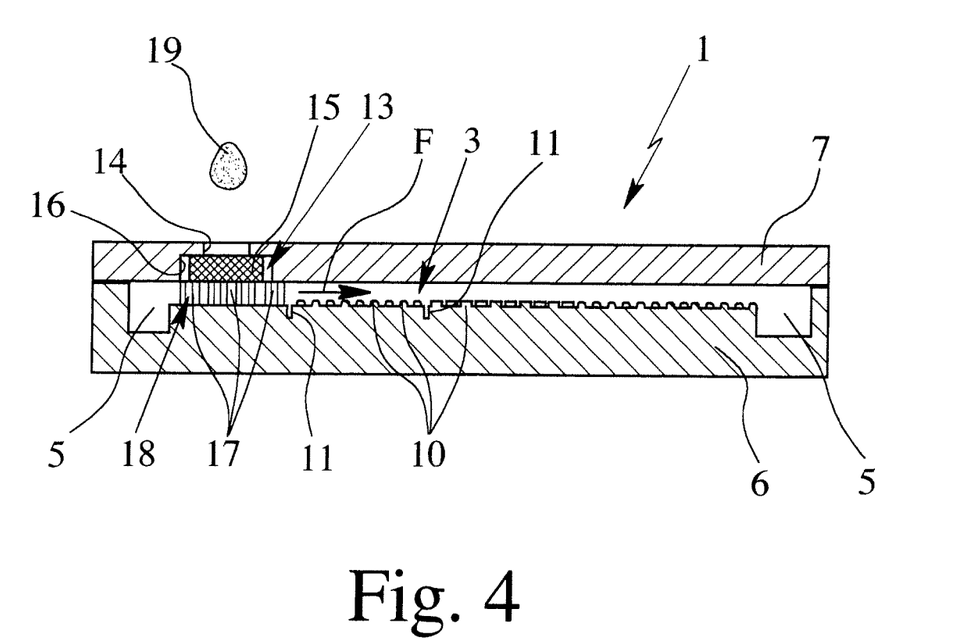

The device 1 has a feed device 13 for receiving blood 19, as shown in FIG. 4. In the embodiment shown, the feed device 13 is formed by an opening, particularly a breach 14, in the cover 7. The device 1 also has an adjoining separator 15 such as a filter, a membrane or the like, for separating off blood plasma as a sample liquid 2.

In the embodiment shown, the separator 15 is inserted in a recess 16 in the cover 7 opening towards the carrier 6 and covering the breach 14.

Preferably, the separator 15 is fixedly connected to the cover 7, e.g., by welding or gluing, or is secured thereto by frictional or interlocking engagement.

The separator 15 is in direct contact with the channel 3, with a flat side in the embodiment shown, and in particular the separator 15 rests on preferably column-like structures 17 or the like in the channel 3 in an inlet region 18 of the channel 3. The structures 17 are preferably provided with wedge-shaped recesses or the like (see the magnified view in FIG. 2b) for guiding the blood plasma or sample liquid 2 by capillary forces from the flat side or outflow side of the separator 15 to the opposite side of the channel —in this case to the bottom 8 of the channel 3 formed by the carrier 6—and thereby totally filling the volume between the bottom 8 and cover 7 or the inlet region 18 with sample liquid 2. However, the structures 17 may also have different geometric shapes and/or may be directly connected to one another.

The structures 17 form a filling device for (totally) filling the channel 3 between the cover 7 and bottom 8 with sample liquid 2. However, the filling device may also be constructed differently, as explained hereinafter with reference to the fourth embodiment.

From the inlet region 18, the sample liquid 2 is sucked further into the channel 3 by capillary forces, as indicated by the main direction of filling F in FIG. 2, after overcoming the first trench 11, in this embodiment.

FIG. 4 shows a schematic longitudinal section through the preferred construction of the proposed device 1 according to the first embodiment, in which a drop of blood 19 supplied thereto is shown for illustration purposes.

The separator 15 may if necessary contain a chemical, particularly a dry chemical, especially for the purpose of allowing or assisting the separation of blood plasma as a sample liquid 2 from the blood 19, as desirable in the embodiment shown, and/or if necessary to allow the lysing of cells. The separation or further conveying are carried out exclusively by capillary forces, in particular.

Preferably, only a single channel 3 adjoins the separator 15, for the purpose of collecting or removing the sample liquid 2. The channel 3 is preferably constructed or intended as an individual capillary. If required, however, the channel 3 may lead in different directions or to different areas or may branch, as explained hereinafter with reference to the second embodiment according to FIG. 5.

Figure 5:
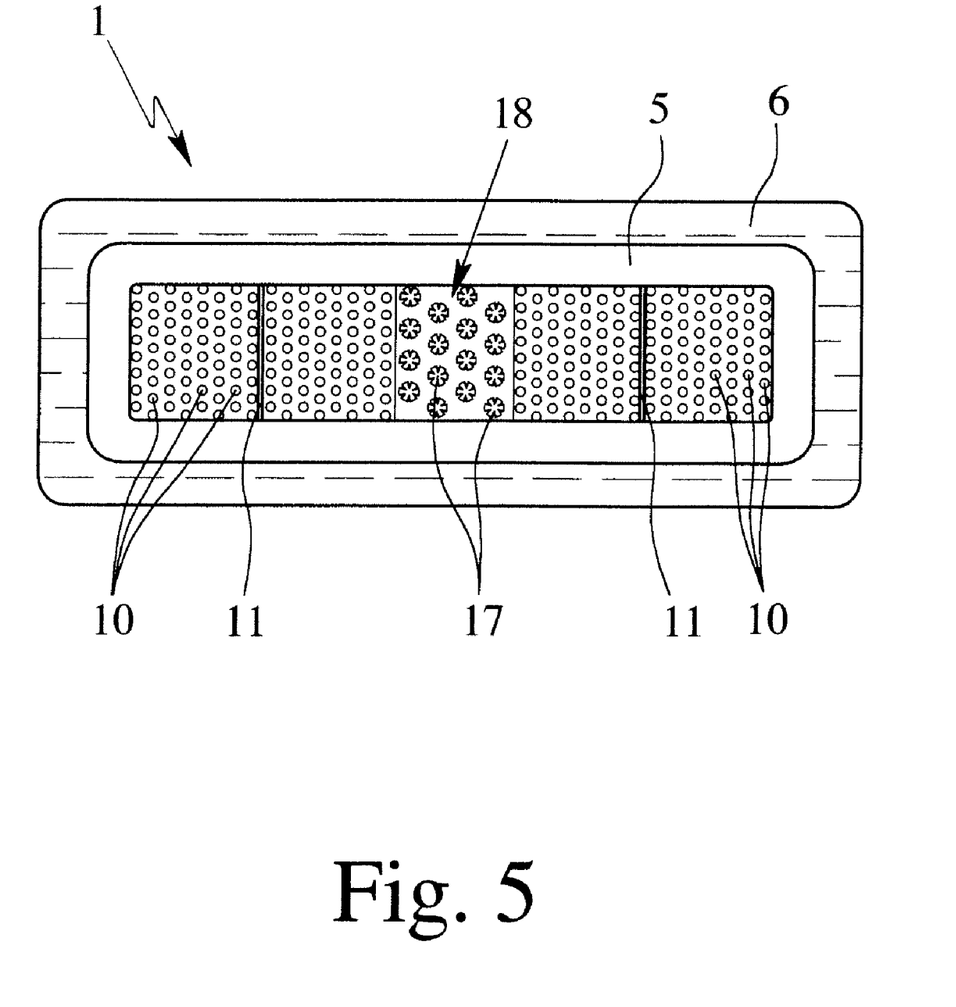
FIG. 5 is a schematic plan view of a carrier of a proposed device according to a second embodiment.

FIG. 5 shows a plan view of the carrier 6 of the device 1 without a cover 7, according to the second embodiment. The channel 3 starting from the feed device 13 or inlet region 18 extends to opposite sides or in opposite directions, for example for the purpose of simultaneously carrying out different investigations, tests or the like. In the embodiment shown, a substantially elongated arrangement is obtained. All kinds of other arrangements are possible, however.

In the second embodiment, preferably the recess 5 is again provided for at least partly guiding the sample liquid 2 in the channel 3 without sidewalls. In particular the recess 5 totally surrounds the entire channel configuration, while the channel 3 may preferably be constructed to be laterally open all round.

In other respects, the remarks made concerning the first embodiment also apply to the second embodiment.

The device 1 according to the first and second embodiments has a venting device for venting the sample liquid 2 in the inlet region 18 transversely with respect to the main filling direction F of the channel 3 and/or transversely with respect to the longitudinal extent of the channel 3, particularly in the main extension plane E of the channel 3. Any air or other gases present can escape laterally from the inlet region 18, as indicated by arrows P in FIG. 3 by way of example. The venting device permits venting of the sample liquid 2 directly at the outflow side of the separator 15, i.e. on the flat side of the separator 15 which is in contact with the inlet region 18 of the channel 3.

In the first and second embodiments the venting device comprises the recess 5 laterally adjoining the channel 3 in order to produce the desired lateral venting. Accordingly, it is sufficient, for the proposed solution, to construct the recess 5 optionally only along the inlet region 18 and, optionally additionally, in the first embodiment along the transverse side of the inlet region 18. The preferred construction of the recess 5 in the first and second embodiments and the guiding of the sample liquid 2 in the channel 3 without any sidewalls, beyond the inlet region 18, along the narrow or longitudinal sides 4 of the channel 3 is advantageous in terms of producing a uniform liquid front V, in terms of preventing lateral advancing of the sample liquid V and in terms of optimizing the venting further along the channel 3, but they are not essential in order to produce the proposed venting in the inlet region 18.

The proposed venting device, in general terms, forms at least one venting path which runs along the outflow side, particularly the flat side, of the separator 15 and at right-angles to the outflow or main filling direction F of the channel 3 with sample liquid 2, to permit optimum filling of the inlet region 18 with sample liquid 2 and in particular to prevent air from being trapped on the outflow side of the separator 15.

In the first and second embodiments, the proposed venting device preferably comprises at least one venting channel 12 which is attached to the recess 5 and connects the recess 5 to the atmosphere. Alternatively, the recess 5 may also open directly into the atmosphere.

The proposed lateral venting in the inlet region 18 may, however, also be achieved by some other method, as described hereinafter, by way of example, in the seventh embodiment, referring to FIGS. 11 and 12.

Other embodiments of the proposed device 1 are described hereinafter, with the emphasis mainly on the essential differences from the previous embodiments. Thus, the foregoing remarks provide complementary or corresponding information.

Figure 6:
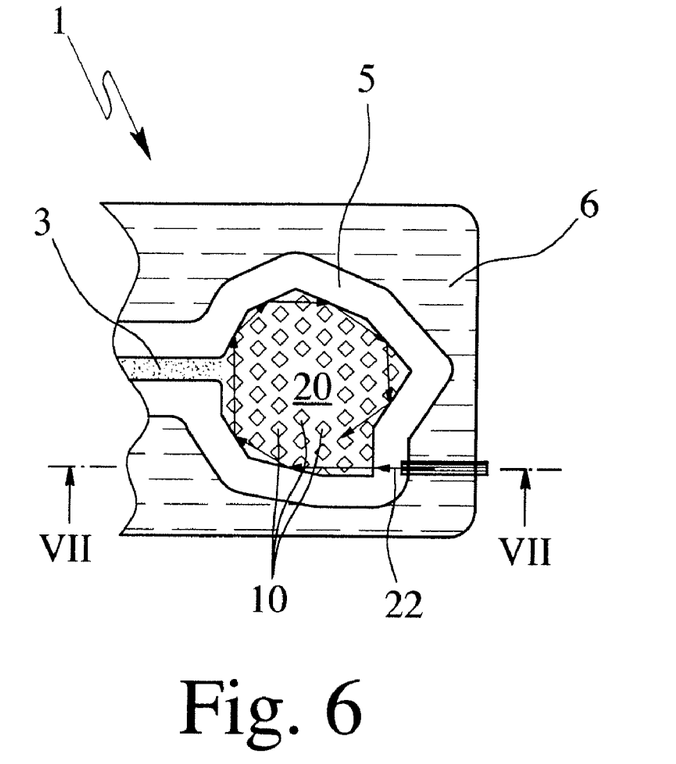
FIG. 6 is a schematic partial plan view of a carrier of a proposed device according to a third embodiment.
Figure 7:
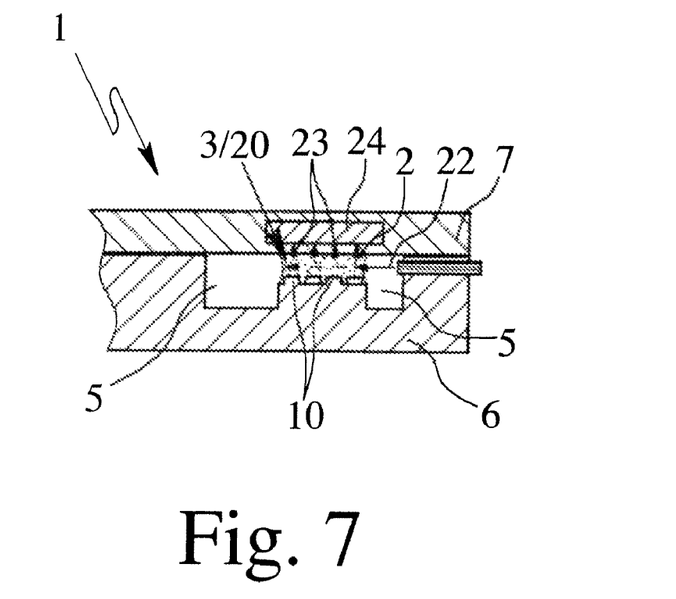
FIG. 7 is a schematic section through part of the device on the line VII-VII in FIG. 6.

FIGS. 6 and 7 show a third embodiment of the proposed device 1 and, specifically, FIG. 6 shows a plan view of the carrier 6 without a cover 7 and FIG. 7 shows a sectional view on the line VII-VII in FIG. 6 with the cover 7 in place. The channel 3 here forms a collecting chamber 20 for the sample liquid 2. The collecting chamber 20 is in turn substantially flat in construction and if necessary comprises the elevations 10 and/or other guide elements or the like indicated.

The device 1 according to the third embodiment comprises a device 21, particularly an optical fiber or the like, for directing light into the sample liquid 2, particularly for fluorescence measurements. The light makes contact with the free surface of the sample liquid 2 in the region of an open side 4 of the channel 3 and because of a suitably steep direction of impact, preferably substantially perpendicular to the surface of the liquid, it enters the sample liquid 2 as indicated by arrow 22. Thus, the interface between gas (air) and sample liquid 2 is used for the air entry. This avoids the light having to be directed by a sidewall which would normally be provided and thereby being scattered in undesirable manner or producing fluorescence.

As shown in FIG. 6, the incoming light beam 22 is preferably reflected several times by total reflection on the interface between the sample liquid 2 and the gas (air). This is achieved by the fact that the angle between the perpendicular to the surface and the incident light beam is greater than the critical angle of the total reflection. The base surface or area of the collecting chamber 20 which is delimited and defined by the surrounding recess 5 is selected accordingly so as to achieve the desired beam guidance and total reflection, in this embodiment by means of a suitable polygonal configuration.

The light 22 shone in is used for fluorescence measurement or for fluorescence spectroscopy. The sample liquid 2, particularly marker molecules or the like contained therein, which are present, for example, as chemicals in the channel 3 and are dissolved by the sample liquid, are excited by a particular wavelength. This leads to the transfer of electrons in the molecules, which after a certain time revert to their original state, while emitting a photon. The radiation emitted is indicated by arrows 23 in FIG. 7 and can be detected by means of a detector 24.

In order to rule out the influence of the elevations 10 or other guiding elements on the incident light beam 22, the plane of the light beam is arranged above or spaced from such structures. Moreover, the plane of the light beam extends at least substantially parallel to the main extension plane or in the main extension plane E of the channel 3 or of the collecting chamber 20.

The irradiation and guiding of light provided ensure substantially total excitation of the sample liquid 2 or marker molecules or the like contained therein and also make it possible to use microstructures such as the elevations 10 or other guide elements.

The grouping of the emitted light beams 23 at right-angles, particularly perpendicularly, to the direction of irradiation 22 is optimum in terms of decoupling from the incident light.

Figures 8, 9A, 9B:
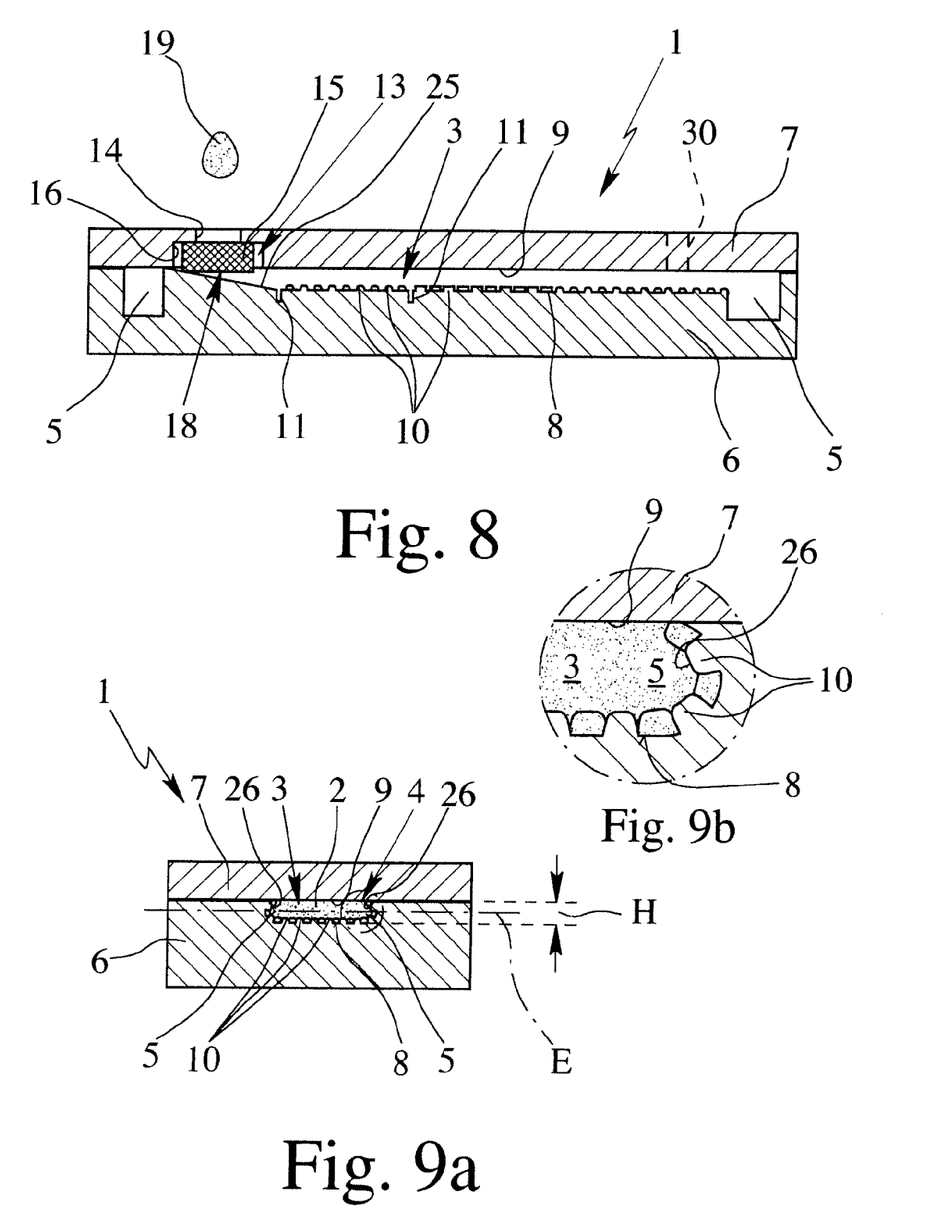

FIG. 8 shows a diagrammatic longitudinal section through a fourth embodiment of the proposed device 1. In contrast to the first embodiment, the filling device for filling the channel 3 comprises, between the two flat sides 8 and 9, a slope or ramp 25 particularly for conducting the blood plasma or sample liquid 2 away from the separator 15 or from the top surface 9 to the opposite bottom surface 8, in order to form a three-dimensional meniscus between the two surfaces or flat sides 8 and 9. This slope or ramp 25 is intended as an alternative or in addition to the structures 17 and correspondingly reduces the channel height H, possibly even to zero. In particular the separator 15 may be in direct contact with the ramp 25 or be supported thereon. The above-mentioned filling device may also be referred to or understood as a device for wetting the cover and base.

The diagrammatic sectional view according to FIG. 9*a* shows a fifth embodiment of the proposed device 1. Here, the recess 5 laterally adjoining the channel 3 can be filled by the sample liquid 2 and is constructed—in particular on the basis of a corresponding rounding of its sidewall 26 and/or by the formation of corresponding guide elements such as elevations 10 or the like, as shown in the magnified detail in FIG. 9*b*—such that the fill speed of the recess 5 in the main filling direction F—i.e. perpendicular to the plane of the drawing in the representation shown in FIG. 9*a*—does not exceed the fill speed of the channel 3, so as to avoid undesirable lateral advancing of the liquid front V. It should be pointed out that in the embodiment shown, the height H of the recess 5 corresponds only to the height H of the channel 3, approximately. Preferably, however, the latter is greater.

Figure 10:
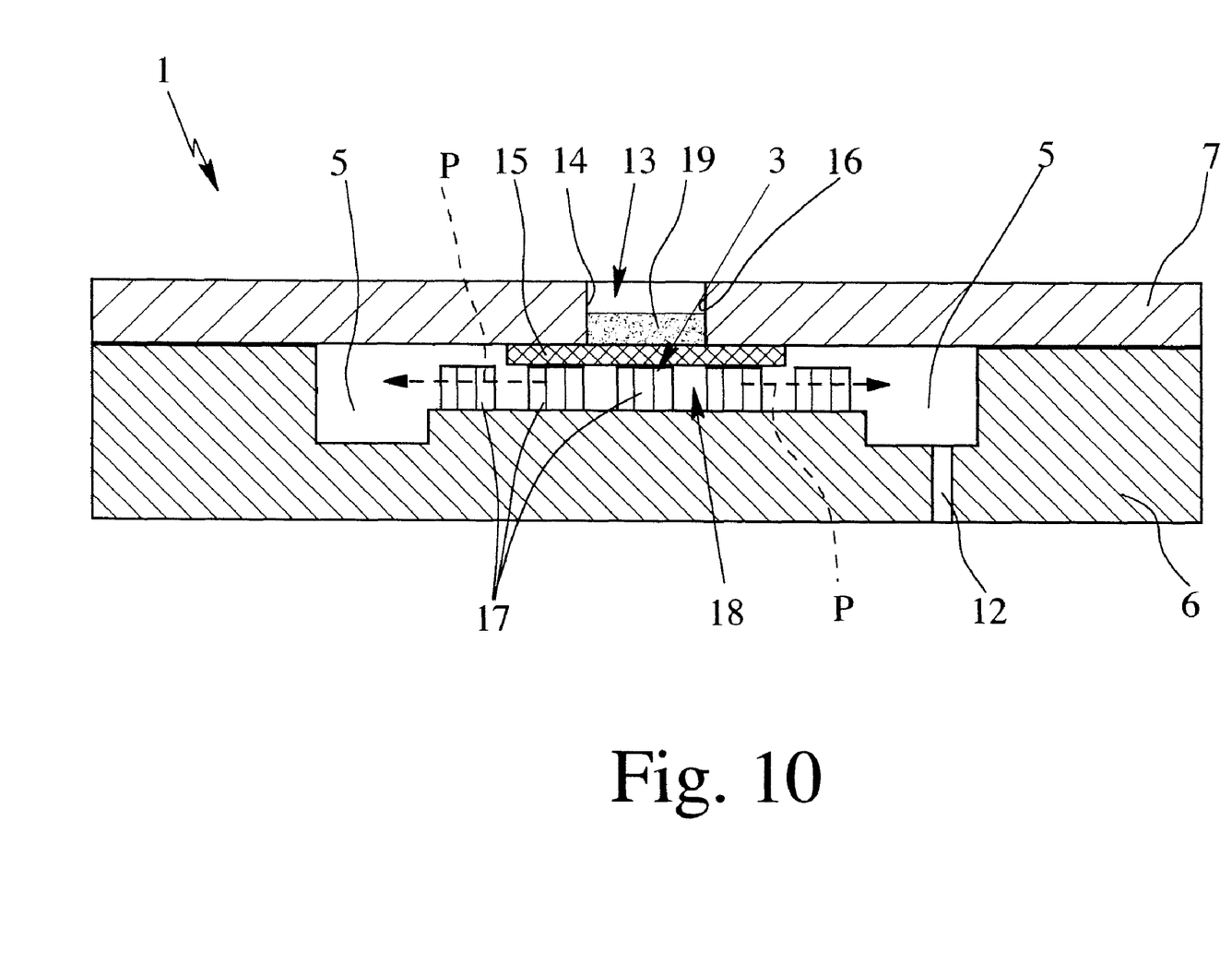
FIG. 10 is a schematic section through a proposed device according to a sixth embodiment.

FIG. 10 shows a sixth embodiment of the proposed device 1 in schematic sectional view in the insertion region 18 at right-angles to the main direction of flow or filling F of the channel 3, i.e., according to FIG. 3.

In the sixth embodiment, the separator 15 has a flat filter element, particularly a thin membrane, which is arranged on the side 9 of the cover 7 facing the channel 3 or its inlet region 18. The membrane preferably covers the breach 14 entirely and is firmly connected to the cover 7 particularly by welding, gluing or the like. The membrane is preferably in direct contact with the fill device arranged underneath, particularly the structures 17 thereof, in order to allow optimum filling of the inlet region 18 with sample liquid 2, as already explained. However, the membrane may also be spaced from the fill device located underneath it.

FIG. 10 illustrates in particular the process for separating blood. Blood 19 is collected from the feed device 13 and preferably covers the separator 15 completely, in order to make full use of the surface area available and thereby achieve the fastest possible separation of blood.

The membrane is designed so that blood cells, particularly red corpuscles, are retained. Preferably the capillarity in the membrane decreases towards the outflow side so as to separate off blood plasma or other blood constituents as a sample liquid 2 and make it available on the outflow side.

The inlet region 18 then receives the separated sample liquid 2, even if the filling device has a lower capillarity than the membrane when the sample liquid 2 flows out of the blood 19 from the inflow side. The inlet region 18 is immediately adjacent to the outflow side or flat side of the separator 15 or membrane, with which it is in full contact, and guides the sample liquid 2—at least after total filling with sample liquid 2—at least substantially parallel to the flat side in the main filling direction F.

The proposed method is characterized in that sample liquid 2 is vented at least in the insertion region 18 at right-angles to the main filling direction F. In particular, the venting is carried out in the main extension plane E of the channel 3 and/or parallel to the flat side of the separator 15. The proposed venting allows total filling of the inlet region 18 and in particular undesirable trapped air and hence potential blockages of the separator 15 are avoided, as explained previously.

Figure 11:
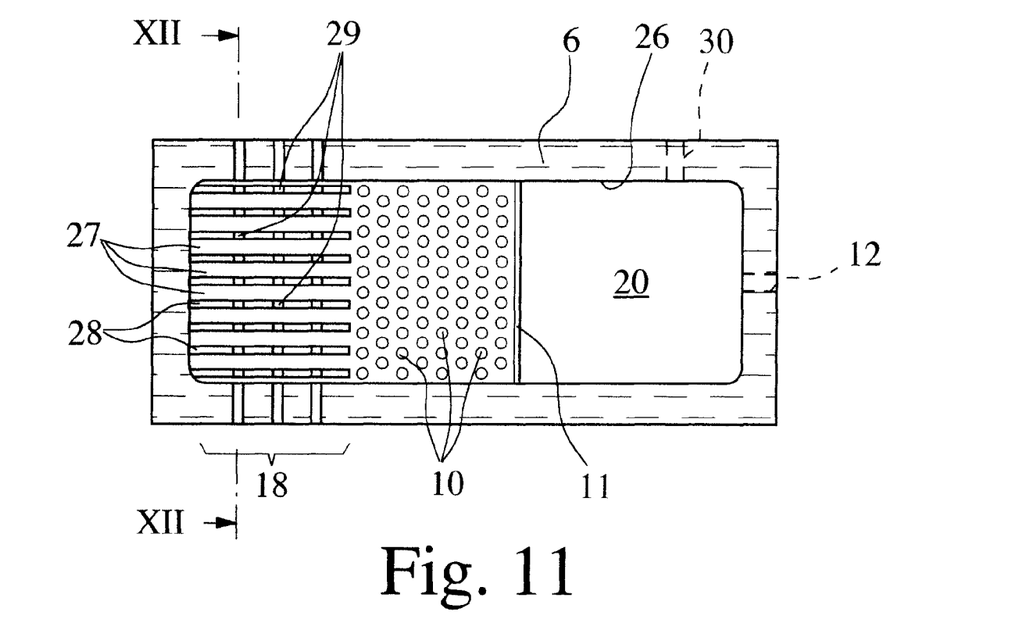
FIG. 11 is a schematic plan view of a carrier of a proposed device according to a seventh embodiment.
Figure 12:
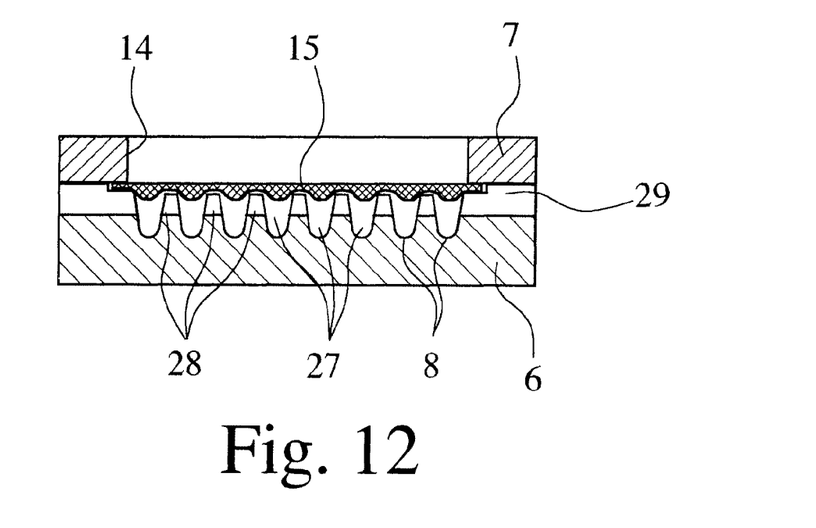
FIG. 12 is a schematic section through the device on the line XII-XII in FIG. 11.

FIGS. 11 and 12 show a seventh embodiment of the proposed device 1 without sample liquid 2. FIG. 11 shows the carrier 6 without a cover 7. FIG. 12 shows a sectional view along the line XII-XII in FIG. 11 with the cover 7 in place.

In contrast to previous embodiments, the channel 3 in the seventh embodiment—at least in the inlet region 18—has a number of individual channels 27 separated from one another by partition walls 28. The individual channels 27 preferably run parallel to one another in the main filling direction F of the channel 3.

The sectional view in FIG. 12 shows that the separator 15, particularly in the form of a flat filter element or a membrane, abuts directly on the partition walls 28 and is optionally domed in the manner of a corrugation into the individual channels 27 or the partition walls 28 can be pressed into the separator 15. This makes it easier to fill the individual channels 27 with sample liquid 2.

Preferably, the individual channels 27 taper in cross-section towards the base 8, i.e. towards the side furthest from the separator 15, in particular in a substantially V-shape in cross-section. This contributes to total filling with sample liquid 2, particularly when the individual channels 27 are of suitable dimensions. The cross-sectional tapering mentioned may also be implemented in the channel 3 independently of the individual channels 27, i.e., in the inlet region 18 and/or in other channel regions. The cross-sectional tapering may also be regarded as a filling device or as a means for (rapidly or totally) filling with sample liquid 2 and may be achieved independently of the present embodiment and independently of the proposed venting.

In the seventh embodiment the sample liquid 2 is preferably not guided in the channel 3 without sidewalls. Rather, the channel 3 is at least substantially bounded at the sides, in this embodiment by an encircling sidewall 26 of the carrier 6, as shown in FIG. 11. If necessary the sidewall 26 according to the fifth embodiment may be rounded and/or provided with means for preventing the lateral advance of the sample liquid 2 in the channel 3, particularly lateral guide elements, elevations 10 or the like, as shown in FIG. 9*b*, in particular.

For the proposed venting the venting device in the seventh embodiment has at least one transverse channel 29 in the inlet region 18, which extends at right-angles to the main filling direction F of the channel 3 and in particular parallel to the outflow side or flat side of the separator 15. In particular, the transverse channel 29 is open over its entire length towards the separator 15 to permit optimum venting.

In the embodiment shown, the venting device comprises a number of transverse channels 29 preferably running parallel to one another to ensure optimum venting of the inlet region 18, even if the sample liquid 2 has not been guided without sidewalls in the inlet region 18. The transverse channels 29 can then be connected to the atmosphere via collecting chambers (not shown) or separate venting channels 12, in order to permit the desired venting.

In the embodiment shown, the transverse channels 29 intersect with the intermediate walls 28 only in an upper region, where necessary, but not over the entire height H of the channel 3. However, this is also possible if necessary.

The cross-sections or external openings of the transverse channels 29 are designed so that sample liquid 2 cannot escape through the transverse channels 29. Alternatively or in addition, capillary stops (not shown), areas with a hydrophobic or hydrophilic coating, materials which are only gas-permeable or the like may be provided to prevent undesirable escape of sample liquid 2 through the transverse channels 29. Alternatively, a certain leakage of sample liquid 2 through the transverse channels 29 may be allowed for, in order to achieve rapid filling of the channel 3 in the inlet region 18 with sample liquid 2 and/or to allow optimum venting.

The proposed venting may be used not only in the devices shown but also in other microfluidic devices for separating sample liquid 2, which are used particularly for separating blood or other particularly biological or medical investigations.

Individual features of the various embodiments may be combined with one another as desired.

The flat sides 8, 9 of the channel 3 may also be of smooth constructions, if desired, and, in particular, do not have texturing, microstructures, guide elements, elevations 10 or the like. For example, the collecting region 20 in the seventh embodiment is smooth in construction.

The proposed devices 1 are suitable for all kinds of tests, investigations or the like. In particular they can be used for immunological or biochemical testing, e.g. of blood 19, blood plasma or the like.

According to an alternative embodiment, the channel 3 may form a plurality of investigating areas or collecting areas 20 which can be filled with the sample liquid 2 one after another. Thus, it is possible, for example, to carry out various investigations one after another and/or to expose the sample liquid 2 to various reagents in succession, particularly dry chemicals, which are dissolved one after another.

According to another alternative embodiment, adjoining a first investigation or collecting region 20 there may be a second investigation or collection region 20, the second region preferably having a substantially higher capillarity, for example by the use of a fleece or the like inserted therein. Thus, after the first region has been filled and in particular after any dry chemical provided therein has been dissolved, the sample liquid 2 can then be sucked or conveyed into the second region, the dry chemical being washed out of the first region and thus, for example, enabling further investigation in the first and/or second region.

Preferably, the capillarity of the channel 3 increases from the inlet region 18 to the other end. This may result in the channel 3 emptying from the inlet region when not enough sample liquid 2 is flowing in. Alternatively, the capillarity in the channel 3 may also be designed to be uniform or to decrease from the inlet region 18 towards the other end, so as to avoid the effect of possible emptying of the channel 3 starting from the inlet region 18.

According to another alternative embodiment, a first chemical, particularly a dry chemical, is provided, preferably in the feed device 13 or separator 15, and at least one second chemical, particularly a dry chemical, is preferably provided in the channel 3 or collecting region 20. This allows effective manipulation or control of the sample liquid 2, blood 19 or the like.

Preferably, for investigating blood plasma, the first chemical is designed so as to prevent or delay coagulation of the blood 19. Thus, for example, EDTA (Ethylene Diamine Tetraacetic Acid) may be provided as the first chemical in order to produce EDTA blood. The EDTA binds the calcium of the blood, which is necessary as Factor IV for blood clotting.

Then, the second chemical, preferably a mixture of chemicals, is used for investigation or for determining one or more parameters in the blood plasma such as glucose, ketones or lactate.

Preferably, for investigating at least one intracellular parameter, such as the hemoglobin level or the calcium level in the blood 19, the first chemical is designed so as to lyse cells such as blood cells and the calcium or the like is released. For this, lysine buffer is used, for example.

Then, the second chemical, preferably a mixture of chemicals, is used for investigating or determining the parameter, particularly the calcium content. A constituent of the mixture, preferably the chelating agent 8-hydroxyquinoline, is used to eliminate from the reaction any magnesium ions which would disrupt the reaction. Another complexing agent, preferably o-cresolphthalein, forms a colored complex with calcium under alkaline conditions.

The extinction of the color complex at a wavelength of 570 nm is proportional to the calcium concentration. It is determined directly in the channel 3 or collecting region 20, or possibly after sampling. However, other measurements or procedures are also possible. In particular, the extinction can also be used at different wavelengths and/or to determine other complexes, parameters or the like. The same is true of other, preferably optical methods of measurement such as fluorescence measurements or the like.

According to yet another alternative embodiment, a sampling opening 30 shown in FIGS. 8 and 11 is provided in the cover 7 and/or in the carrier 6, to allow the sampling of the sample liquid 2, particularly the separated blood plasma or the like. The sampling opening 30 is preferably connected to an at least relatively large-capacity storage region 20 or the like in the channel 3, to allow a desired or sufficient sampling volume to be held in readiness.

What is claimed is:

1. Device for collecting blood and separating blood constituents, comprising a cover and a carrier, a feed device for collecting the blood, a separator for separating blood constituents as sample liquid, a channel receiving the sample liquid, an inlet region of the channel adjoining an underside of the separator for receiving the separated sample liquid from the separator, and a venting device for venting the sample liquid in the inlet region laterally at right-angles to the main filling direction from the inlet region into the channel, wherein the venting device has a recess laterally adjacent to the channel and wherein the venting device has at least one venting channel in the carrier of the device connected to the recess.

2. Device according to claim 1, wherein the venting device for venting the sample liquid in the inlet region is formed in the main extension plane of the channel.

3. Device according to claim 1, wherein the venting device comprises at least one transverse channel in the inlet region extending at right-angles to the main direction of filling of the channel with sample liquid.

4. Device according to claim 1 wherein the channel has surfaces with a spacing which produce capillary forces by which the channel receives the sample liquid.

5. Device according to claim 1 wherein said venting device vents the sample liquid in the inlet region at right-angles to the longitudinal extent of the channel.

6. Device according to claim 1, wherein the venting device for venting the sample liquid in the inlet region is formed along a flat side of the separator.

7. Device according to claim 1, wherein the venting device for venting the sample liquid in the inlet region is formed at right-angles to the direction of flow of the sample liquid through the separator.

8. Device according to claim 1, wherein the venting device has a recess laterally adjacent to the channel.

9. Device according to claim 8, wherein the venting device has at least one venting channel adjacent to the recess.

10. Device according to claim 8, wherein the recess runs along at least one of opposite open narrow sides and longitudinal sides of the channel.

11. Device according to claim 8, wherein the device has a carrier and a cover between which the channel and recess are formed.

12. Device according to claim 1, wherein the separator is of planar construction, the inlet region being immediately adjacent to a flat side of the separator and the main filling direction of the channel extending parallel to the flat side.

13. Device according to claim 1, wherein the separator has a filter for separating blood plasma as a sample liquid.

14. Device according to claim 1, wherein the separator has a membrane for separating blood plasma as a sample liquid.

15. Device according to claim 1, wherein the channel has a cross section which tapers from the separator towards the base.

16. Device according to claim 15, wherein the cross-section of the channel is a V-shape.

17. Device according to claim 1, wherein the channel has a plurality of individual channels, at least in the inlet region.

18. Device according to claim 1, wherein the channel is formed by two opposing surfaces which are substantially planar.

19. Device according to claim 1, wherein the channel is of open construction and the sample liquid can be guided along the channel without sidewalls.

20. Device according to claim 1, wherein the channel has a substantially rectangular cross-section at right-angles to at least one of the main direction of filling with sample liquid and the longitudinal dimension of the channel.

21. Device according to claim 1, wherein the height of the channel is less than the width of the channel.

22. Device according to claim 1, wherein the height of the channel is less than the width of the channel at least by a factor of 5.

23. Device according to claim 1, wherein the capacity of the channel is less than 1 ml.

24. Device according to claim 1, wherein the channel forms at least one reservoir for the sample liquid.

25. Device according to claim 1, wherein the channel contains a chemical.

26. Device according to claim 25, wherein said chemical is a dry chemical.

27. Device according to claim 1, wherein the channel has at least one guide element for influencing the filling with the sample liquid.

28. Device according to claim 27, wherein the guide elements have a spacing and size at least one of which varies as a function of the respective distance from an inlet for the sample liquid into the channel.

29. Device according to claim 27, wherein the channel has at least one trench as a guide element, extending transversely with respect to the main direction of filling of the channel for forming a temporary liquid stop for evening out the liquid front of the sample liquid.

30. Device according to claim 1, wherein the channel has regularly distributed elevations as guide elements.

31. Device according to claim 1, wherein the feed device includes a first chemical for lysing blood cells.

32. Device according to claim 31, wherein the first chemical is in the form of a dry chemical and can be dissolved by the liquid supplied to the feed device.

33. Device according to claim 1, wherein the channel is provided with at least one second chemical.

34. Device according to claim 33, wherein the second chemical is in the form of a dry chemical which can be dissolved by the sample liquid.

35. Device according to claim 33, wherein the second chemical allows the Ca content to be determined.

36. Device according to claim 33, wherein the second chemical contains a complexing agent to form a colored complex.

37. Device according to claim 1, wherein adjoining the separator is a single channel for receiving and discharging the sample liquid, said single channel leading in different directions.

38. Device according to claim 1, including a detector mounted on said channel for measuring scattered radiation.

39. Device according to claim 1, including a sampling device for sampling sample liquid.

40. Device for collecting blood and separating blood constituents, comprising a feed device for collecting the blood, a separator for separating blood constituents as sample liquid, a channel receiving the sample liquid, an inlet region of the channel adjoining an underside of the separator for receiving the separated sample liquid, and a venting device for venting the sample liquid in the inlet region laterally at right-angles to a main filling direction from the inlet region into the channel, wherein the device has a filling device for filling the channel with sample liquid between opposing surfaces in the inlet region which delimit the channel, wherein the filling device comprises at least one structure projecting from one of said surfaces which creates a recess therearound, the separator resting on said at least one structure.

41. Device according to claim 40, wherein the filling device has a ramp which reduces the height of the channel in the inlet region.

42. Device for collecting blood and separating blood constituents, comprising a feed device for collecting the blood, a separator for separating blood constituents as sample liquid, a channel receiving the sample liquid, an inlet region of the channel adjoining an underside of the separator for receiving the separated sample liquid, and a venting device for venting the sample liquid in the inlet area laterally at right-angles to a main filling direction from the inlet region into the channel, including means for directing light into the sample liquid, said means for directing light being directed at a free surface of the sample liquid in the region of an open side of the channel.

43. Device according to claim 42 wherein the means for directing light directs light into the sample liquid for fluorescence measurements.

44. Device according to claim 43, wherein the light directed inwards can be reflected off the interface between the sample liquid and channel wall.

45. A method of separating blood constituents or blood plasma as a sample liquid from blood using a planar separator, the sample liquid separated off being collected by a channel, the inlet region of which adjoins the flat side of the separator and conveys the sample liquid parallel to the flat side in a main filling direction, said sample liquid being vented at least in the inlet region at right-angles to the main filling direction.

* * * * *